US006965052B2

(12) United States Patent
Beckman et al.

(10) Patent No.: US 6,965,052 B2
(45) Date of Patent: Nov. 15, 2005

(54) SYNTHESIS OF N-VINYL FORMAMIDE (75) Inventors: Eric J. Beckman, Aspinwall, PA (US); Tody M. Chapman, Pittsburgh, PA (US); Cedrick Gilbert Favero, Givors (FR); Christopher C. Capelli, Kenosha, WI (US); Harold E. Swift, Gibsonia, PA (US)

(73) Assignees: University of Pittsburgh, Pittsburgh, PA (US); SNF SA, Andreziux Cedex (FR)

( * ) Notice: Subject to any disclaimer, the term of this patent is extended or adjusted under 35 U.S.C. 154(b) by 0 days.

(21) Appl. No.: 10/652,104

(22) Filed: Aug. 29, 2003

(65) Prior Publication Data

US 2004/0186319 A1 Sep. 23, 2004

Related U.S. Application Data (60) Provisional application No. 60/407,077, filed on Aug. 30, 2002.

(51) Int. Cl.$^7$ ............................................. C07C 233/03
(52) U.S. Cl. ............................ 564/215; 525/43; 526/72; 502/402
(58) Field of Search ........................... 564/215; 526/72; 525/43; 502/402

(56) References Cited

U.S. PATENT DOCUMENTS

| | | | | |
|---|---|---|---|---|
| 4,804,686 A | * | 2/1989 | Regnier et al. ................ | 521/28 |
| 4,942,259 A | | 7/1990 | Parris | |
| 5,059,713 A | | 10/1991 | Armor | |

FOREIGN PATENT DOCUMENTS

| | | | |
|---|---|---|---|
| DE | 3500773 | * | 7/1985 |
| DE | 4116266 A1 | | 3/1992 |
| DE | 4438366 A1 | | 5/1998 |
| EP | 0361514 A2 | | 4/1990 |
| EP | 0362804 A2 | | 4/1990 |
| EP | 0440226 A2 | | 8/1991 |
| FR | 2 558 156 | | 7/1985 |
| JP | 61097309 A | | 5/1986 |
| JP | 63-190862 | * | 8/1988 |
| JP | 03182946 B | | 7/2001 |
| JP | 03314417 B | | 8/2002 |
| JP | 03319007 B | | 8/2002 |
| WO | WO 2004/020395 A1 | | 3/2004 |

OTHER PUBLICATIONS

Chang et al, Macromolecules, 1993, 26, 4814–4816.*
Parris, G.E. and Armor, J.N, Applied Catalysis, vol. 78, pp 65–78 (1991).
Database WPI, Section Ch, Week 200263, Derwent Publications Ltd., London, GB; AN 1994–354704.
Database WPI, Section Ch, Week 200139, Derwent Publications Ltd., London, GB: AN 1994–245670.
Database WPI, Section Ch, Week 200259, Derwent Publications Ltd., London, GB: AN 1994–186386.

* cited by examiner

*Primary Examiner*—Shailendra Kumar
(74) *Attorney, Agent, or Firm*—Bartony & Hare, LLP (57) ABSTRACT

A process to produce N-vinylformamide includes the steps of: reacting hydroxyethyl formamide with a reactant including at least one cyclic anhydride group to form an ester, and dissociating (or cracking) the ester to synthesize N-vinylformamide and a compound including at least one diacid group. The ester can be dissociated using heat. The reactant including at least one cyclic anhydride group can, for example, be succinic anhydride, maleic anhydride, phthalic anhydride, a polymer including at least one cyclic anhydride group, or a solid support to which at least one cyclic anhydride group is covalently tethered. Preferably, the cyclic anhydride is regenerated from the diacid formed in the synthesis of the ester by heating the diacid to dehydrate the diacid. The temperature required to dehydrate diacid groups is preferably higher than the temperature use to dissociate the ester.

29 Claims, 6 Drawing Sheets

Fig. 1

Fig. 2 i. K$_2$CO$_3$ (0.5 mol% cf. Formamide);
   10-15 C for 3h
   70 C for 24h ii.

iii. Heat

Fig. 3A

Succinic Anhydride

Phthalic Anhydride

Maleic Anhydride

General Cyclic Anhydride

SYNTHESIS OF N-VINYL FORMAMIDE

CROSS-REFERENCE TO RELATED APPLICATION

The present application claims benefit of U.S. Provisional Patent Application Ser. No. 60/407,077, filed Aug. 30, 2002, the disclosure of which is incorporate herein by reference.

BACKGROUND OF THE INVENTION

The present invention relates to the synthesis of N-vinylformamide, and particularly, to the synthesis of N-vinylformamide using cyclic anhydride reagents.

N-vinylformamide (NVF) is a monomer with potentially useful properties in that it free-radically polymerizes to produce water-soluble poly(N-vinylformamide) (PNVF) and also undergoes controlled radical polymerization using RAFT methodology. Badesso, R. J.; Nordquist, A. F.; Pinschmidt, Jr. R. K.; and Sagl, D. J. "Hydrophilic polymers: performance with Environmental Acceptance", Glass, E.; Ed.; America Chemical Society, Washington, D.C., 1995, p489. PNVF is probably the most practical precursor for preparation of poly(vinylamine). Because vinyl amine is unstable and hence cannot be maintained, PNVF is likely the best route to the generation of polyvinyl amine, a useful and less toxic alternative to polyacrylamide and other cationic, water-soluble polymers PNVF is easily hydrolyzed under basic or acidic conditions to form poly(vinylamine).

There are three known commercial routes to NVF. For example, BASF, at its Ludwigshafen, Germany site, reacts acetaldehyde with HCN, then formamide, forming the cyanoethyl formamide (FAN). FAN is then "cracked" to NVF plus HCN, where the latter is recycled. The BASF Ludwigshafen, Germany site is one of the few sites in the world skilled in HCN chemistry. As this highly toxic chemical cannot be transported, the process is most likely restricted to Ludwigshafen.

Mitsubishi developed a process whereby acetaldehyde is reacted with formamide to form hydroxyethyl formamide (HEF) using either acid or base catalysis. HEF is then reacted with methanol to form methoxyethyl formamide (MEF) using an acid catalyst with the loss of water. HEF is finally cracked to methanol and NVF, and the NVF purified. It has been reported that the NVF material synthesized by this method, exhibited lower than desired purity.

Air Products developed an alternative route to NVF wherein HEF is reacted with additional formamide (over a solid acid catalyst) to form the ethylidene bisformamide (BIS) plus water. BIS is then cracked (pyrolyzed) to form NVF plus formamide (wherein the latter is recycled). The NVF is then vacuum distilled. It is quite important in the operation of this process to minimize the hydrolysis of formamide (creating ammonia that fouls the catalyst) during BIS formation. Obviously the presence of water during this reaction creates problems.

It is very desirable to develop alternative routes to the synthesis of N-vinylformamide.

SUMMARY OF THE INVENTION

In one aspect, the present invention provides a process to produce N-vinylformamide including the steps of: reacting hydroxyethyl formamide with a reactant including at least one cyclic anhydride group to form an ester, and dissociating (or cracking) the ester to synthesize N-vinylformamide and a compound including at least one diacid group. The ester can be dissociated using heat. The reactant including at least one cyclic anhydride group can, for example, be succinic anhydride, maleic anhydride, phthalic anhydride, a polymer including at least one cyclic anhydride group, or a solid support to which at least one cyclic anhydride group is covalently tethered. Preferably, the cyclic anhydride is regenerated from the diacid formed in the synthesis of the ester. The anhydride can, for example, be regenerated by heating the diacid to dehydrate the diacid or by passing the diacid over a dehydration catalyst. Homogeneous or heterogeneous dehydration catalysts can be use (for example, zeolite, resins acids, vanadium oxide, phosphoric oxide or any other dehydration catalyst as known to those skilled in the art). The conditions required to dehydrate diacid groups are preferably different from the conditions used to dissociate the ester. For example, in the case that heat is used to dehydrate the diacid, the temperature required for dehydration can be higher than the temperature used to dissociate the ester.

As used herein, the term "polymer" refers to a compound having multiple repeat units (or monomer units) and includes the term "oligomer," which is a polymer that has only a few repeat units. The term polymer also includes copolymers which is a polymer including two or more dissimilar repeat units (including terpolymers-comprising three dissimilar repeat units-etc.).

Although the reaction can be carried out without the use of solvent, a solvent can be added. Suitable solvents include aprotic or aromatic solvents. Preferably, such solvents do not interfere with the reactions of the present invention. NVF can be used as a solvent in the process. Examples of other suitable solvents include, but are not limited to, toluene, xylene, acetonitrile, ether, dimethyl sulfoxide and/or acetaldehyde. Suitable solvents also include isoparafin-like solvents, including, but not limited to, the products sold by Exxon Corporation under the name ISOPAR®, which are generally non-toxic in nature.

In one embodiment a solvent (for example, NVF) is used in which NVF is soluble and in which a polymer including at least one cyclic anhydride group is at least partially soluble. However, the polymer including at least one ester group formed in the synthesis and the polymer including at least one diacid group formed in the synthesis have no or limited solubility in the solvent.

Generally, polymers used in the process of the present invention preferably include or incorporate a plurality of cyclic anhydride groups. For example, a copolymer of methyl vinylether and maleic anhydride can be used. The methyl vinylether/maleic anhydride copolymer can, for example, have a weight average molecular weight in the range of approximately 190,000 to 3,000,000. The polymer can also be a reaction product of an alpha olefin or a mixture of alpha olefins with maleic anhydride. In one embodiment, the alpha olefin is a C-18 alpha olefin and the co polymer has a molecular weight of at least 20,000. The polymer can also be a methyl vinylether/maleic anhydride/decadiene copolymer. Another suitable polymer for use in the present invention is a copolymer of styrene and maleic anhydride. The styrene/maleic anhydride copolymer can, for example, have a weight average molecular weight of at least 2000.

In one embodiment the polymer is a solid in the reaction. For example, the polymer can be a porous crosslinked solid. Preferably, the porous polymer has a relatively high surface area.

In one embodiment in which the reactant including at least one cyclic anhydride group is a solid support to which at least one cyclic anhydride group is covalently tethered, the solid support is silica.

In another embodiment, acetaldehyde, formamide and the reactant including at least one cyclic anhydride group are mixed in a single reaction vessel, wherein hydroxyethyl formamide is formed in the reaction vessel to react with the reactant including at least one cyclic anhydride group.

In another aspect, the present invention provides a process to produce N-vinylformamide including the step of: mixing acetaldehyde, formamide and a source of anhydride in a single reaction vessel. The anhydride reacts with hydroxyethyl formamide formed in the reaction vessel to form an ester as described above. The ester is dissociated (or cracked) as described above to synthesize N-vinylformamide and a compound including at least one diacid group. In one embodiment, the source of anhydride is a reactant including at least one cyclic anhydride group. The reactant including at least one cyclic anhydride group can, for example, be succinic anhydride, maleic anhydride, phthalic anhydride, a polymer including at least on cyclic anhydride group, or a solid support to which at least one cyclic anhydride group is covalently tethered. In one embodiment, the acetaldehyde to formamide mole ratio can, for example, be at least two. However, lower acetaldehyde to formamide mole ratios can be used. An acid or base catalyst can be used in the reaction to make hydroxyethyl formamide.

The process of the present invention can be carried out continuously or batchwise. Suitable reactors include, but are not limited to, tubular reactors and stirred tank reactors.

In still another aspect, the present invention provides a reagent including at least on cyclic anhydride group covalently tethered to a solid support. The solid support can, for example, be silica. Preferably, a plurality of cyclic anhydride groups are tethered to the solid support.

The present invention, along with the attributes and attendant advantages thereof, will best be appreciated and understood in view of the following detailed description taken in conjunction with the accompanying drawings.

DETAILED DESCRIPTION OF THE INVENTION

Figure 1:
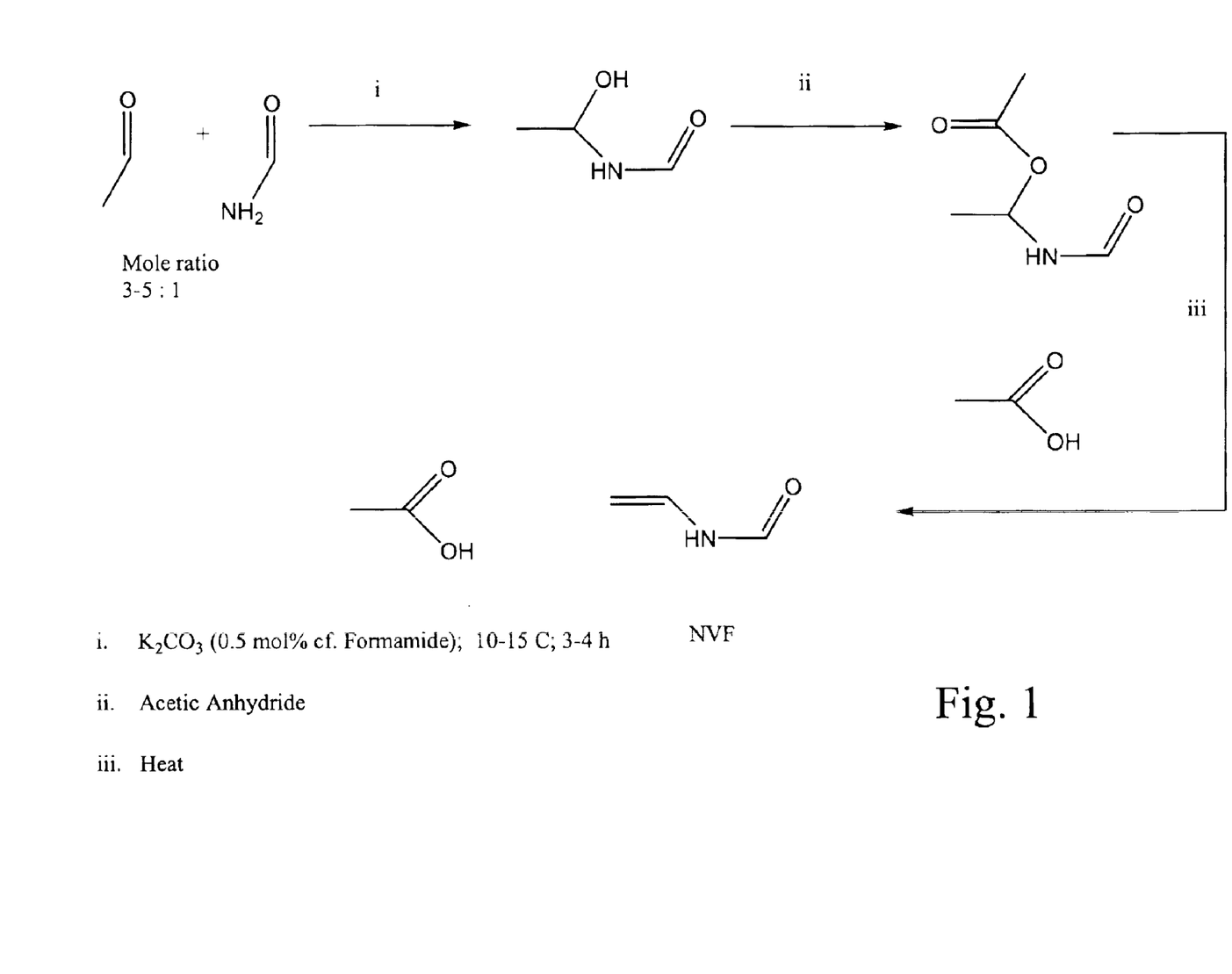
FIG. 1 illustrates the sequential synthesis of NVF via first synthesizing HEF, reacting HEF with acetic anhydride and cracking the resulting ester to form NVF.

FIG. 1 illustrates a sequential synthesis of NVF developed at Air Product wherein HEF is first synthesized via the reaction of acetaldehyde and formamide. See Parris, G. E. and Armor, J. N, Applied Catalysis, Vol. 78, pp 65–78 (1991). HEF is then reacted with acetic anhydride to form an HEF adduct The resulting HEF adduct/ester is subjected to heat (cracked) to form NVF.

Figure 2:
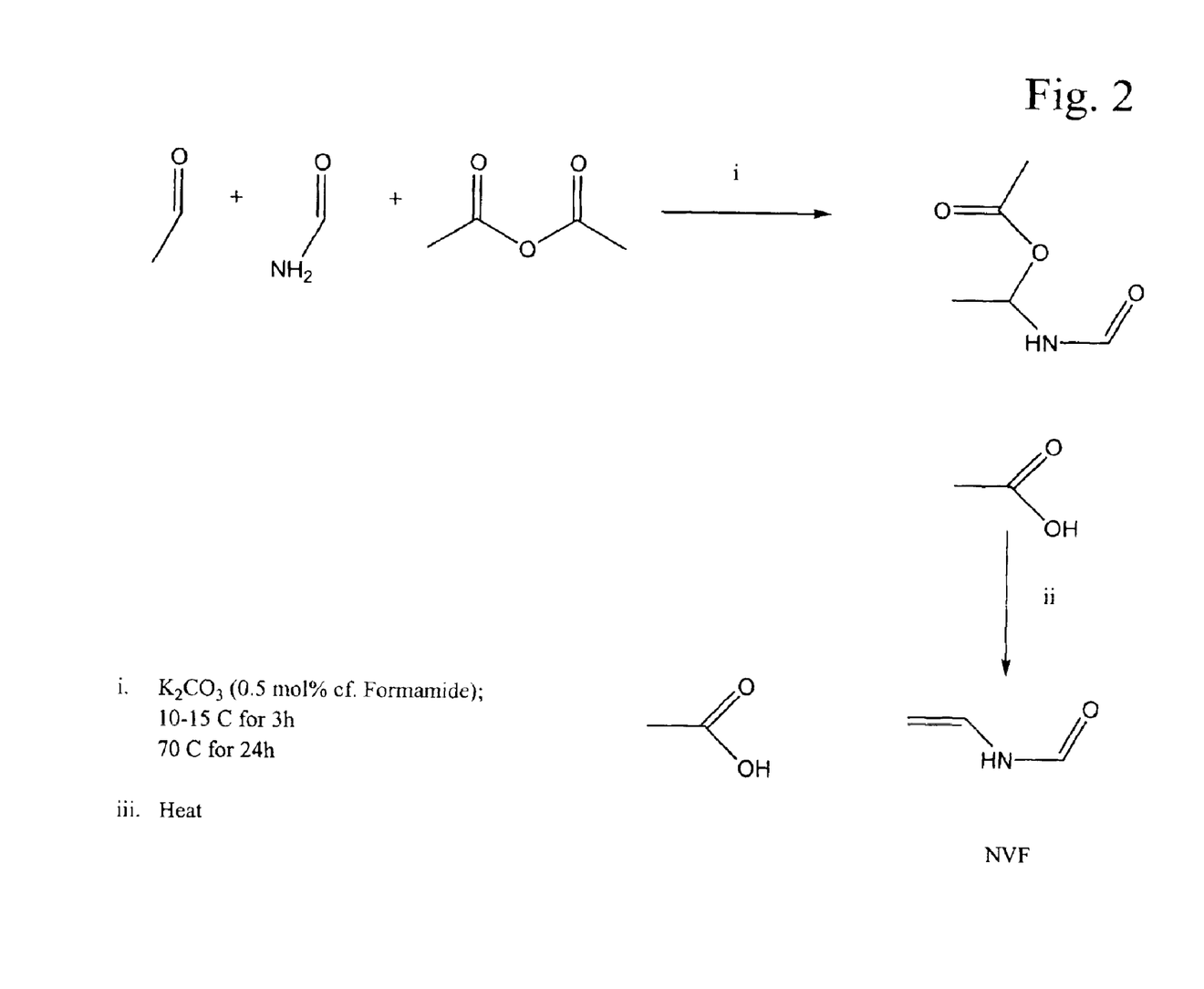
FIG. 2 illustrates a one pot synthesis of NVF of the present invention wherein acetaldehyde, formamide and acetic anhydride are mixed.

The present inventors have discovered that NVF can also be formed via a single reaction mixture including acetaldehyde, formamide and an anhydride such as acetic anhydride as illustrated in FIG. 2. The resulting HEF adduct is cracked to form NVF, The one-pot or single reactor synthesis of the present invention can, for example, provide cost savings by reducing unit operation costs. As expected from studies of the sequential synthetic route, the reaction rate increased in the one-pot synthesis with increasing temperature. As monitored by IR, for example, the anhydride peak was found to disappear in 42 hours at room temperature (approximately 22° C.), in 23 hours at 50° C., and in 7.5 hours at 100° C., in the sequential synthesis. IR analysis of a one-pot synthesis according to FIG. 2 also demonstrated disappearance of the anhydride peak over time. The temperature of the reaction of the present invention is generally approximately 0° C. to 150° C., preferably approximately 20° C. to 100° C., and more preferably approximately 30 to 80° C. In the studies of the present invention, a reaction temperature in the range of approximately 30° C. to approximately 80° C. was used. Either an acid catalyst or a base catalyst can be used. If an acid catalyst is used, only a catalytic amount of acid is preferably added to the reaction mixture (for example, 0.001–0.2 times the stoichiometry to HEF). Example of suitable acid catalysts include, but are not limited to, sulfuric acid, paratoluenesulfonic acid, methane sulfonic acid, amberlyst or any other acidic ion exchange resin. If a base catalyst is used, a nearly stoichiometric amount of base can be required (for example, 0.2 to 5 times the stoichiometry to HEF). Suitable homogeneous catalyst for use in the present invention include, but are not limited to, triethylamine, pyridine and caustic catalysts. In general, any basic ion exchange catalyst such as Amberlite, Lewatit, Puralit is also suitable. Basic zeolites can also be suitable in certain cases.

In each of the synthetic routes of FIGS. 1 and 2, however, two moles of acetic acid are produced during the synthesis of one mole of NVF. One mole of acetic acid is produced in the synthesis of the HEF adduct, and another mole of acetic acid is produced during cracking of the HEF adduct. Acids such as acetic acid destabilize NVF. Moreover, the removal of such acids via, for example, distillation is difficult as the relative volatilities of the acid and NVF are similar.

Figure 3A:
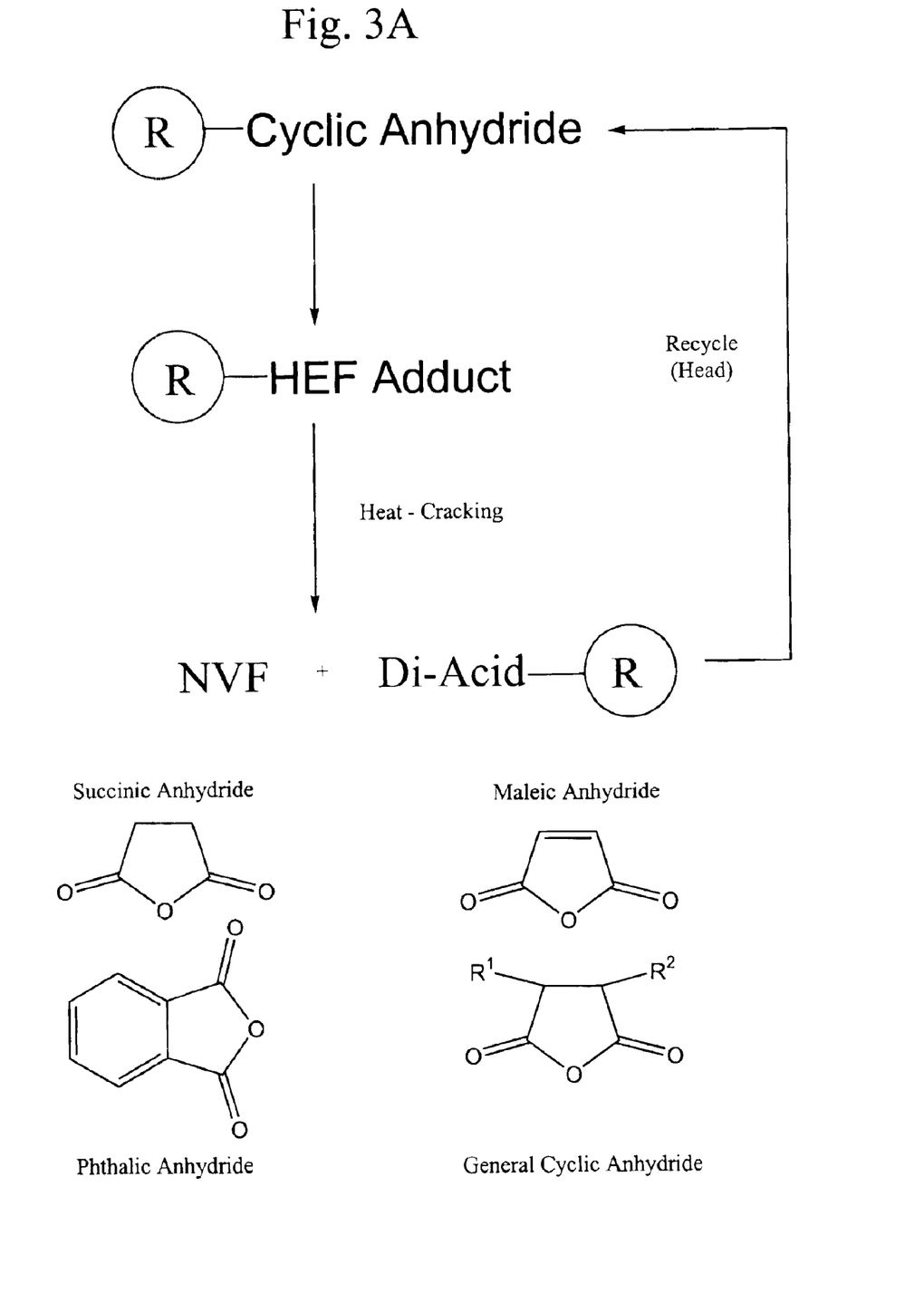
FIG. 3A illustrates an embodiment of a synthetic route to NVF of the present invention wherein a cyclic anhydride is reacted with HEF to form an HEF-adduct, which is subsequently cracked to form NVF.
Figure 3B:
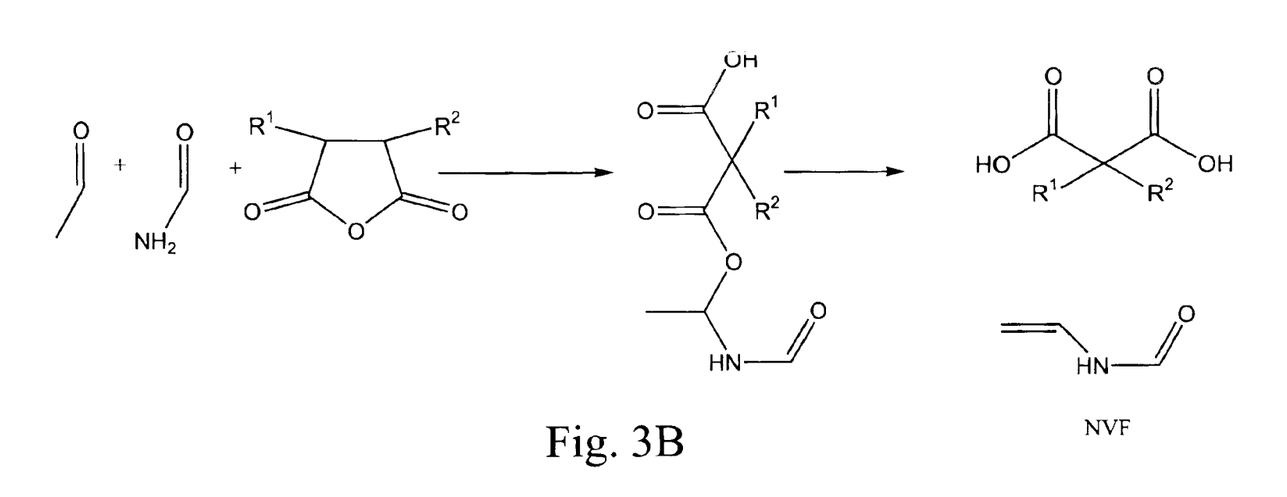
FIG. 3B illustrates a sequential synthesis under the general synthetic route of FIG. 3A.
Figure 3C:
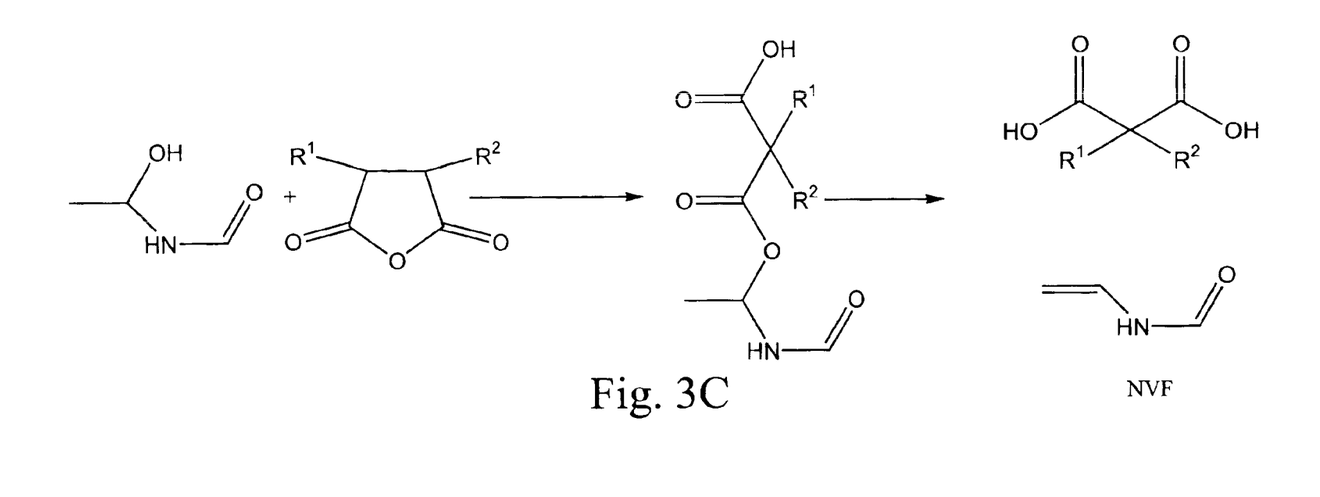
FIG. 3C illustrates a one-pot synthesis under the general synthetic route of FIG. 3A.

In another aspect of the present invention as illustrated, for example, in FIGS. 3A through 3C, an alternative route to the synthesis of NVF is provided in which a cyclic anhydride is reacted with HEF. In the synthetic route of the present invention, HEF is reacted with a cyclic anhydride to form the corresponding ester (HEF adduct). The ester is then cracked to NVF plus the corresponding diacid under very mild conditions (for example, temperatures less than 25° C.). The temperature of cracking is generally approximately 0° C. to 250° C., preferably approximately 20° C. to 200° C., and more preferably approximately 60 to 180° C.

While one can form NVF from a simple, non-cyclic anhydride (for example, acetic anhydride as illustrated in FIGS. 1 and 2), this reaction produces a very soluble acid byproduct which ultimately destabilizes the NVF as described above. Once again, the removal or separation of the resultant acids using non-cyclic anhydrides is very difficult. In the synthetic route of the present invention, relatively heavy cyclic anhydrides (many of which are commercially available or readily synthesized from commercially available reagents) are reacted with HEF to produce the corresponding HEF adduct and a diacid. No byproduct is produced. The diacid generated during the cracking step is generally less soluble than, for example, acetic acid formed in the synthetic route of FIGS. 1 and 2. Indeed, in several embodiment of the present invention in which a solubilized source of cyclic anhydride is used, the diacid may precipitate as a solid as it is formed. Examples of cyclic anhydrides suitable for use in the synthetic processes of the present invention include maleic anhydride, succinic anhydride and phthalic anhydride (the structures of which are set forth in FIG. 3A).

The diacid formed in the synthesis of the present invention can be recycled and dehydrated to reform the anhydride. This recycling dehydration step can generally occur at a temperature higher than the temperature used to crack the HEF adduct and results in the formation of water. The temperature of the dehydration is generally approximately 100° C. to 450° C., preferably approximately 120° C. to 300° C., and more preferably approximately 150 to 250° C. A dehydration catalyst can also be used to lower the temperature of dehydration, but is preferably not present in the cracking step to avoid the undesirable formation of water when NVF is formed. Suitable dehydration catalysts include homogeneous and heterogeneous catalysts (for example, zeolite, resins, acids, vanadium oxide, phosphoric oxide and any other dehydration catalyst as known to those skilled in the art). Unlike several current synthetic routes to NVF, the water produced in the recycling step of the present invention is formed "offline" and will not result in hydrolysis of the formamide precursor or the NVF product. Moreover, the synthetic route of the present invention requires less stringent conditions than current synthetic routes and hence can provide a product of increased purity. NVF of increased purity, for example, allows for generation of higher molecular weight poly(NVF)).

Figure 4:
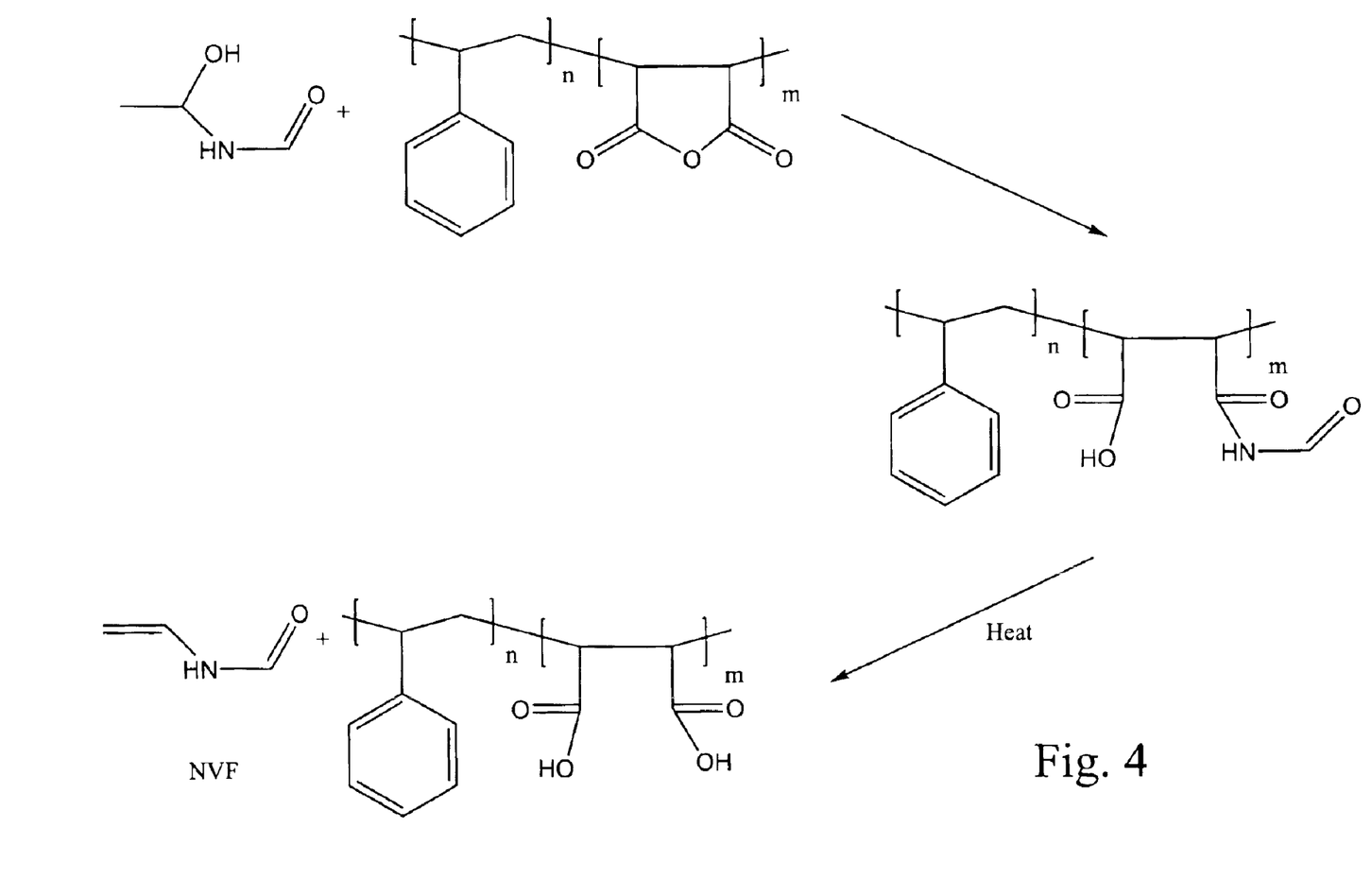
FIG. 4 illustrates an embodiment of a synthetic route of the present invention in which a poly(styrene-co-maleic anhydride) copolymer is reacted with HEF.

Various "substituted" cyclic anhydrides can be used in the synthetic route of the present invention to further decrease any adverse effects upon the NVF product of the diacid produced in the synthesis of the present invention. Generally, the use of such substituted cyclic anhydrides preferably reduces the solubility of the resulting diacid in the process solvent and/or facilitates the separation of that diacid from the NVF product. For example, in one embodiment a polymeric material including cyclic anhydride groups can be reacted with HEF. In the embodiment of FIG. 4, for example, a copolymer of styrene and maleic anhydride was used as the source of cyclic anhydride. In this embodiment, the cracking reaction produced liquid NVF and generally insoluble or reduced solubility polymer including diacid groups.

Polymers including cyclic anhydride groups for use in the present invention can be soluble in a solvent in which the reaction is carried out. As HEF is a solid at room temperature, the adduct of HEF and the anhydrides used in the present invention may in some cases also be a solid. Thus, the use of a solvent/co-solvent may be required. As any solvent used in the processes of the present invention is typically ultimately required to be separated from the NVF product, it is advantageous to use NVF as a process solvent in the reactions of the present invention. In using NVF as the process solvent, a recycle stream can be taken from an intermediate point in the process to provide the needed solvent. In the case that a soluble polymer including cyclic anhydride groups are used, the resulting polymer containing diacid groups preferably readily precipitates from solution (for example, upon formation or upon addition of a co-solvent or other additive) and/or is preferably readily otherwise separable from the NVF product. Separation of the polymer including diacid groups from NVF is typically readily achieved given the substantial difference in molecular weight between NVF and the polymer including diacid groups.

Because of the great difference in the volatilities of the diacid and NVF, it is possible, for example, to separate the monomer by a short residence time flash stripping leading to an enhanced quality of monomer. Melt crystallization can also be used to separate the monomer from a third solvent used to remove the diacid. Conditions of cracking (temperature and vacuum) can also be adjusted to flash the monomer as soon as it is formed. If the solid ester is heated at, for example, 150° C. and 2 mm Hg, NVF will naturally be formed in a gaseous state and can be condensed as pure NVF in another vessel.

Additionally, polymers including cyclic anhydride groups that are insoluble in the process solvent (for example, solid polymers) can also be used in the present invention. As reactions of HEF with such insoluble polymers will occur only at the surface of the polymer, the surface area of such polymer is preferably relatively high. Such polymers can, for example, be synthesized as porous polymeric beads in a manner similar to the synthesis of, for example, polymeric ionic exchange beads as known in the art. In one embodiment, for example, divinyl benzene can be used as a crosslinker in a copolymer of divinyl benzene, styrene and maleic anhydride to produce a high surface area, porous polymer bead including cyclic anhydride groups for use in the reactions of the present invention. Preferably, the surface area is maximized. A surface area of, for example, at least 10 $m^2/g$ is preferred. As the resulting diacid is covalently bound to the solid polymer, the detrimental effect of the diacid groups upon the NVF product is not substantial.

Figure 5A:
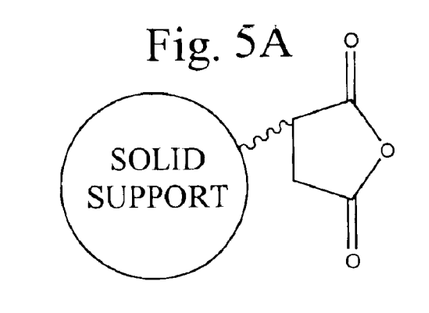
FIG. 5A illustrates a cyclic anhydride covalently tethered to a solid support for use in the synthetic methods of the present invention.
Figure 5B:
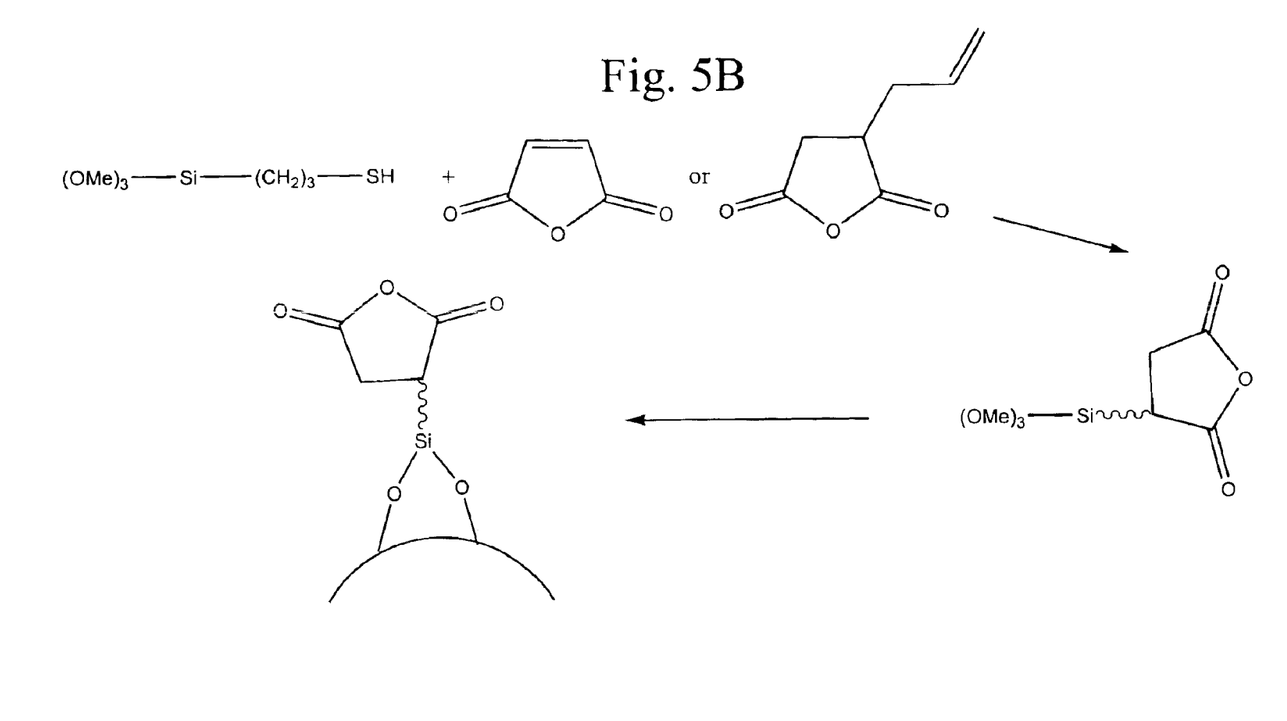
FIG. 5B illustrates one embodiment of a synthetic route to the synthesis of a silica supported cyclic anhydride.

As illustrated in, for example, FIG. 5A, in another embodiment of the present invention, cyclic anhydride reagents for use the present invention can be immobilized upon a solid support (for example, a polymeric bead or a silica support). FIG. 5B illustrates one embodiment of immobilization of a cyclic anhydride group on silica. Supports other than silica (for example, glass, alumina and activated carbon can also be used to immobilize the cyclic anhydride reagents of the present invention.

The cyclic anhydrides of the present invention can be reacted in either a sequential synthesis or a one-pot synthesis to form NVF as described above. In the generalized formula of a cyclic anhydride suitable for use in the present invention, $R^1$ and $R^2$ can independently be chosen from a very broad range of substituents. It is believed that electron withdrawing groups (for example, $NO_2$, halo group (for example, Cl, F or Br) and—CN) may result in a faster reaction time. In the case that a polymer including or incorporating cyclic anhydride groups is used, $R^1$ and $R^2$ can, for example, be styrene or vinyl repeat groups. Virtually any vinyl monomer (for example, vinyl ether) is suitable for use in synthesizing polymers suitable for use in the present invention. Maleic anhydride typically copolymerizes in an alternative fashion. Thus $R^1$ and $R^2$ can be the same in the case of copolymerization of maleic anhydride. Styrene is an attractive comonomer as formation of crosslinked porous beads is readily achieved using styrene as a comonomer.

A number of polymeric anhydrides suitable for use in the present invention are commercially available. For example, a methyl vinylether/maleic anhydride copolymer is available from ISP Chemicals under the name GANTREZ® in the molecular weight range of 190,000 to 3,000,000. The polymer has the general formula:

A methyl vinylether/maleic anhydride decadiene crosslinked polymer is also available from ISP Chemicals under the name STABILEZE®.

A copolymer of a C-18 alpha olefin with maleic anhydride have the following formula:

is available from Chevron Phillips under the produce name PA-18 Polyanhydride Resin.

Styrene maleic anhydride copolymers having the general formula:

are available, for example, from Sartomer of Exton, Pa.

Experimental Examples

In the studies of the present invention, some of the quantities were varied between experiments but the quantities set forth in the examples below are representative values and scales. No attempt was made to optimize any of the reactions studied.

(1) One-Pot Reaction of Acetaldehyde, Formamide and Acetic Anhydride i) No solvent: Acetaldehyde [21 ml; 0.377 mol], formamide [5 ml; 0.126 mol; containing 0.5 mol % $K_2CO_3$] and acetic anhydride [6 ml; 0.062 mol] were added to a flask and stirred at approximately 10° C. for 2 h. The reaction was allowed to warm to room temperature over 1 h and then heated to 70° C. IR monitoring was done throughout, demonstrating disappearance of the anhydride peaks and indicating the synthesis of the HEF adduct.

ii) With solvent: The same method as i) was followed but in addition, 40 ml of isooctane was added at the start of the reaction. Two layers were present throughout the reaction. IR monitoring was done throughout, demonstrating disappearance of the anhydride peaks and indicating the synthesis of the HEF adduct.

(2) Production of NVF Using Poly(Styrene-Co-Maleic Anhydride)

Sequential addition: Acetaldehyde [5.66 ml; 0.10 mol] was dissolved in dioxane [20 ml] at 10° C. Formamide [01 ml; 0.025 mol; containing 0.5 mol % $K_2CO_3$] was added dropwise, and the reaction was stirred at 10-15° C. for 2 h. Poly(styrene-co-maleic anhydride) [68 wt % styrene; Mn~1700] [8.29 g] was dissolved in dioxane [50 ml] and the solution added to the reaction. IR monitoring was done throughout the reaction. Anhydride peaks substantially reduced but did not completely disappear in IR over the time the reaction was carried out. Synthesis of NVF was confirmed by NMR.

(3) Preparation of Tethered Anhydride i) As illustrated in Scheme 1 below, Allylsuccinic anhydride [0.67 g; 0.005 mol], (3-mercaptopropyl-trimethoxysilane [2.8 g; 0.014 mol] and AIBN [50 mg] were dissolved in chloroform [60 ml] and refluxed overnight. Solid product was filtered off, and the solvent was removed from the filtrate to leave a yellow oil.

ii) The product from i) was added to a stirred suspension of silica gel [8 g; surface area ~500 m²/g] in toluene [200 ml] and stirring was continued at room temperature for approximately 20 h. The silica (i.e. tethered anhydride) was then filtered off and washed with toluene.

(4) Reaction of tethered anhydride

HEF and the tethered anhydride were reacted at 80° C. in dioxane. The silica support was then filtered from the reaction mixture. The remaining reaction components were then heated at 100° C. for approximately 6 hours.

Scheme 1

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A process to produce N-vinylformamide including the steps of: reacting hydroxyethyl formamide with a reactant including at least one cyclic anhydride group to form an ester, and dissociating the ester to synthesize N-vinylformamide and a compound including at least one diacid group.

2. The process of claim 1 wherein the reactant including at least one cyclic anhydride group is succinic anhydride, maleic anhydride, phthalic anhydride, a polymer including at least one cyclic anhydride group, or a solid support to which at least one cyclic anhydride group is covalently tethered.

3. A process of claim 1 wherein the cyclic anhydride is regenerated from a diacid formed in the synthesis of the ester by dehydrating the diacid.

4. The process of claim 1 further comprising where NVF is used as a solvent.

5. The process of claim 1 further comprising where toluene or acetaldehyde is used as a solvent.

6. The process of claim 2 wherein a polymer including at least one cyclic anhydride group is used.

7. The process of claim 6 further including the step of regenerating the polymer including at least one cyclic anhydride group by heating the polymeric material containing at least one diacid group to a temperature sufficiently high to dehydrate diacid groups.

8. The process of claim 7 wherein the temperature used to dehydrate diacid groups is higher than a temperature use to dissociate the ester by heat.

9. The process of claim 6 further comprising where NVF is used as a solvent.

10. The process of claim 6 further comprising where toluene or acetaldehyde is used as a solvent.

11. The process of claim 6 where a solvent is used in which NVF is soluble and in which the polymer including at least one cyclic anhydride group, the polymer including at least one ester group and the polymer including at least one diacid group having no or limited solubility in the solvent.

12. The process of claim 6 where polymer includes a plurality of cyclic anhydride groups and is a copolymer of methyl vinylether and maleic anhydride.

13. The process of claim 12 where in the methyl vinylether/maleic anhydride copolymer has a weight average molecular weight in the range of approximately 190,000 to 3,000,000.

14. The process of claim 6 wherein the polymer is a reaction product an alpha olefin or a mixture of alpha olefins with maleic anhydride.

15. A process of claim 14 the alpha olefin is a C-18 alpha olefin and wherein the polymer has a molecular weight of at least 20,000.

16. The process of claim 6 where the polymer is a methyl vinylether/maleic anhydride decadiene copolymer.

17. The process of claim 6 wherein the polymer is a copolymer of styrene and maleic anhydride.

18. The process of claim 16 wherein the copolymer has a weight average molecular weight of at least 2000.

19. The process of claim 6 wherein the polymer is a solid in the reaction.

20. The process of claim 19 wherein the polymer is a porous crosslinked solid.

21. The process of claim 20 wherein the polymer is a crosslinked polymer including styrene and maleic anhydride repeat units.

22. The process of claim 2 wherein the reactant including at least one cyclic anhydride group is a solid support to which at least one cyclic anhydride group is covalently tethered.

23. The process of claim 22 wherein the solid support is silica.

24. The process of claim 1 wherein acetaldehyde, formamide and the reactant including at least one cyclic anhydride group are mixed in a single reaction vessel, hydroxyethyl formamide being formed in the reaction vessel to react with the reactant including at least one cyclic anhydride group.

25. A process to produce N-vinylformamide including the steps of: mixing acetaldehyde, formamide and a source of anhydride in a single reaction vessel, dissociating an ester formed by a reaction between the source of anhydride and hydroxyethyl formamide formed in the reaction vessel to synthesize N-vinylformamide and a compound including at least one diacid group.

26. The process of claim 25 wherein the source of anhydride is a reactant including at least one cyclic anhydride group.

27. The process of claim 26 wherein the reactant including at least one cyclic anhydride group is succinic anhydride, maleic anhydride, phthalic anhydride, a polymer including at least one cyclic anhydride group, or a solid support to which at least one cyclic anhydride group is covalently tethered.

28. The process of claim 25 wherein the acetaldehyde to formamide mole ratio is at least two.

29. A process of claim 25, where a base or an acid catalyst is used in the reaction to make hydroxyethyl formamide.

\* \* \* \* \*